United States Patent
Nakamura et al.

(10) Patent No.: US 10,845,314 B2
(45) Date of Patent: Nov. 24, 2020

(54) GAS SENSING ELEMENT AND METHODS OF MAKING THE SAME

(71) Applicant: Nitto Denko Corporation, Osaka (JP)

(72) Inventors: Koichi Nakamura, Rockledge, FL (US); Nahid Mohajeri, Rockledge, FL (US); Yu-chu Chen, Evanston, IL (US); Kujtim Bizati, Lakewood, NJ (US); Shinji Inokuchi, Tinton Falls, NJ (US)

(73) Assignee: Nitto Denko Corporation, Osaka (JP)

( * ) Notice: Subject to any disclaimer, the term of this patent is extended or adjusted under 35 U.S.C. 154(b) by 159 days.

(21) Appl. No.: 16/070,610

(22) PCT Filed: Feb. 16, 2018

(86) PCT No.: PCT/US2018/018486
§ 371 (c)(1),
(2) Date: Jul. 17, 2018

(87) PCT Pub. No.: WO2018/152398
PCT Pub. Date: Aug. 23, 2018

(65) Prior Publication Data
US 2020/0124538 A1    Apr. 23, 2020

Related U.S. Application Data

(60) Provisional application No. 62/460,490, filed on Feb. 17, 2017, provisional application No. 62/483,521, filed on Apr. 10, 2017.

(51) Int. Cl.
*G01N 21/78* (2006.01)
*G01M 3/22* (2006.01)
(Continued)

(52) U.S. Cl.
CPC ............ *G01N 21/783* (2013.01); *G01M 3/04* (2013.01); *G01M 3/22* (2013.01); *G01N 31/223* (2013.01);
(Continued)

(58) Field of Classification Search
CPC .. G01N 21/783; G01N 31/223; G01N 33/005; G01N 33/0062; G01N 33/0027; G01N 33/0009; G01M 3/04; G01M 3/22
See application file for complete search history.

(56) References Cited

U.S. PATENT DOCUMENTS 4,309,520 A    1/1982    Blizzard
5,248,739 A    9/1993    Schmidt et al.
(Continued)

OTHER PUBLICATIONS

Hartmann et al,"Passive Leak Detection Using Commercial Hydrogen Colorimetric Indicator" NREL Technical Report Sep. 2016, pp. 1-27 (Year: 2016).*
(Continued)

*Primary Examiner* — Dennis White
(74) *Attorney, Agent, or Firm* — IPUSA, PLLC

(57) ABSTRACT

A gas sensing element includes a gas detection layer including a chemochromic pigment, with modifications towards enhancing shelf-life performance and false detection performance before use. The gas detection layer has an adhesion of greater than or equal to 0.2 N/25 mm. Also described are methods of making the aforedescribed element to attain enhanced shelf-life performance and false detection performance.

15 Claims, 4 Drawing Sheets

ILLUSTRATION PURPOSES ONLY,
NOT TO SCALE

(51) Int. Cl.
*G01N 31/22* (2006.01)
*G01N 33/00* (2006.01)
*G01M 3/04* (2006.01)

(52) U.S. Cl.
CPC ....... *G01N 33/005* (2013.01); *G01N 33/0027* (2013.01); *G01N 33/0062* (2013.01)

(56) References Cited

U.S. PATENT DOCUMENTS

| | | | |
|---|---|---|---|
| 5,430,293 A | 7/1995 | Sato et al. | |
| 5,508,509 A * | 4/1996 | Yafuso | G01N 31/223 250/216 |
| 5,849,073 A * | 12/1998 | Sakamoto | B82Y 30/00 106/437 |
| 7,851,758 B1 | 12/2010 | Scanlon et al. | |
| 8,652,993 B2 | 2/2014 | Mohajeri | |
| 2003/0186013 A1 | 10/2003 | Dhaler et al. | |
| 2007/0224081 A1* | 9/2007 | Bokerman | G01N 21/783 422/400 |
| 2008/0213527 A1 | 9/2008 | Nonaka et al. | |
| 2010/0253376 A1 | 10/2010 | Grosse Bley et al. | |
| 2011/0300296 A1* | 12/2011 | Sherman | C08G 77/442 427/208.4 |
| 2012/0040180 A1 | 2/2012 | Husemann et al. | |
| 2013/0005045 A1 | 1/2013 | Captain et al. | |
| 2014/0028459 A1 | 1/2014 | Solomon | |
| 2014/0032160 A1 | 1/2014 | Rella et al. | |
| 2014/0051567 A1 | 2/2014 | Mohajeri | |
| 2014/0170535 A1 | 6/2014 | Yano et al. | |

OTHER PUBLICATIONS

International Search Report for PCT/US18/18486 dated Apr. 25, 2018.
International Search Report for PCT/US18/18531 dated Apr. 20, 2018.
International Search Report for PCT/US18/18532 dated Apr. 20, 2018.
Office Action dated Nov. 29, 2019 issued with respect to the related U.S. Appl. No. 16/070,068.
Office Action dated Mar. 10, 2020 issued with respect to the related U.S. Appl. No. 16/070,068.
Office Action dated Mar. 30, 2020 issued with respect to the related U.S. Appl. No. 16/070,069.
Gas Leak Detector is Simple and Inexpensive, Nasa Tech Brief, Dec. 1966, p. 1 (Year: 1966).
Office Action dated Jul. 16, 2020 issued with respect to the related U.S. Appl. No. 16/070,068.
Office Action dated Jul. 30, 2020 issued with respect to the related U.S. Appl. No. 16/070,069.

* cited by examiner

ILLUSTRATION PURPOSES ONLY,
NOT TO SCALE

GAS SENSING ELEMENT AND METHODS OF MAKING THE SAME

The present application claims priority to U.S. Provisional Patent Application No. 62/460,490, filed on Feb. 17, 2017, and U.S. Provisional Patent Application No. 62/483,521, filed on Apr. 10, 2017, the contents of which are incorporated herein by reference in their entirety.

TECHNICAL FIELD

The disclosed embodiments relate to a gas sensing element (also referred to herein as "gas detection element").

BACKGROUND ART

Technology has been developed for gas detection tape as described in U.S. Pat. Nos. 8,591,818; 8,652,993; and 8,703,642 for high temperature environments.

The conventional hydrogen gas detection sheet includes forming a hydrogen gas detection layer on a backing material, as described in, for example, U.S. Pat. No. 8,591,818. However, a hydrogen gas detection sheet having such a configuration does not have substantial adhesion to its measurement targets (i.e., junctions, flanges, valves, etc. to be detected for gas leakage).

Therefore, when actually using the conventional hydrogen gas detection sheet, an auxiliary tape and an adhesive, etc., are used to fix the hydrogen gas detection sheet to the measurement target. That is, the hydrogen gas detection sheet is fixed to the measurement target, for example, by attaching the adhesive tape as an auxiliary tape across the hydrogen gas detection sheet and the measurement target, in a state in which one side of the hydrogen gas detection layer of the hydrogen gas detection sheet is in contact with the setting side of the measurement target.

However, the above method may be a factor that causes a decrease in the workability at the site. Furthermore, by the above method, a gap may be formed between the measurement target and the hydrogen gas detection layer, and this may be a factor that hampers accurate measurements.

Therefore, in order to address the above problem, one approach may be to form the hydrogen gas detection sheet by setting the hydrogen gas detection layer and an adhesive layer on the backing material during manufacturing.

However, a problem with the above configuration is that the structure of the hydrogen gas detection sheet may be complicated by setting the adhesive layer. Particularly, the adhesive layer is not involved in the hydrogen gas detection, and is essentially an unnecessary member. Rather, if an adhesive layer is present on the hydrogen gas detection layer, this adhesive layer may hamper the movement of hydrogen gas to the hydrogen gas detection layer, and the hydrogen gas may not be accurately detected.

Furthermore, in a conventional gas detection element, for example, in a situation where the concentration of the measurement target gas is low, there are cases where the color change, which occurs when contact is made with the measurement target gas, is insufficient.

In this case, in particular, when the measurement target is located away from the examining staff, it is difficult for the examining staff to determine whether there is any color change in the gas detection element.

Furthermore, for example, at a plant, etc., where hydrogen gas is used, there are cases where the piping, through which the hydrogen gas flows, is arranged at a location that is difficult to visually confirm. In these cases, in order to detect whether gas leakage has occurred, it would take significant amounts of labor and cost.

Thus, there remains a need for an improved gas detection tape composition embodiment that reduces the problems described above.

SUMMARY OF INVENTION

As a result of the need for new materials and processes, a new gas detection tape comprising chemochromic materials and a method for manufacturing the aforementioned tape can be realized to facilitate passive and efficient gas level detection.

In some embodiments, a pressure sensitive adhesive ("PSA") gas detection element is described, where the element can comprise chemochromic composition including a palladium oxide, palladium hydroxide, or palladium salts, dispersed within a polymer matrix of a siloxane crosslinked by free radical transfer reaction.

In some elements, the siloxane can comprise polydimethylsiloxane and polydimethyldiphenylsiloxanes with different percentages of phenyl content. Some initiators can be a peroxide, such as benzoyl peroxide or 2,4-dichlorobenzoyl peroxide.

In some elements, the element can further comprise a backing to form a tape. In some embodiments, the backing can comprise a polymer such as polyimide, fluorinated ethylene propylene, polyethylene, polytetrafluoroethylene, or polyethylene terephthalate. In some embodiments, the backing can be resistant to ultraviolet (UV) radiation.

In some embodiments, methods of producing a pressure sensitive gas detection adhesive are described. In some embodiments, the method can comprise: (1) contacting a treatment liquid and a chemochromic composition, the treatment liquid comprising a siloxane precursor and a peroxide initiator; and (2) heating the treatment liquid to a temperature sufficient to activate the initiator so that the precursor is crosslinked to create a polymer matrix containing the chemochromic composition. In some embodiments, the initiator can comprise a peroxide, such as benzoyl peroxide or 2,4-dichlorobenzoyl peroxide. In some embodiments, the siloxane precursor can comprise polydimethylsiloxane and polydimethyldiphenylsiloxanes with different percentages of phenyl content. In some embodiments, the chemochromic composition can comprise one or more palladium-oxide-based chemochromic elements.

For some methods, the heating step can be done at a temperature with a profile within the range of 120° C. to 200° C. for 1 to 3 minutes. In some embodiments, the heating step can further comprise an additional step of removing any solvent from the treatment liquid before the primary heating step by heating at a temperature within the range of 25° C. to 100° C. For example, in the case of 25° C., the heating time is preferably approximately 10 minutes, and in the case of 100° C., the heating time is preferably approximately 30 seconds.

Some methods can further comprise the step of applying the contacted treatment liquid and chemochromic composition in a layer on a backing, whereby the result is a tape. In some embodiments, the backing can comprise a polymer such as polyimide, polypropylene, fluorinated ethylene propylene, ethylene tetrafluoroethylene, polyethylene, polytetrafluoroethylene, perfluoroalkoxy alkanes, or polyethylene terephthalate. In some embodiments, the backing can be resistant to ultraviolet radiation.

Some methods additionally comprise the step of exposing the polymer matrix to an oxygen-containing atmosphere. In some embodiments, the step of exposing to an oxygen-containing atmosphere may comprise exposing to air. For some embodiments, the step of exposing the polymer matrix to an oxygen-containing atmosphere can comprise using an oxygen permeable release liner. In some embodiments, the step of exposing the pressure sensitive adhesive to an oxygen-containing atmosphere can comprise maintaining the physical parameters of the adhesive material to less than amount sufficient to allow contact of the resulting adhesive to the surrounding air.

In some embodiments, a gas sensing element is described. The gas sensing element includes a gas detection layer including a pigment, wherein the gas detection layer has an adhesion of greater than or equal to 0.2 N/25 mm.

In some embodiments, a gas detection layer is described. The gas detection layer includes a pigment, wherein the gas detection layer has an adhesion of greater than or equal to 0.2 N/25 mm.

In some embodiments, a gas sensing element is described. The gas sensing element includes a gas detection layer including a pigment, wherein the pigment indicates an irreversible color reaction with respect to reducing gas, on a first surface of the gas detection layer, a translucent layer is disposed (also referred to as "backing" or "backing layer" herein), and the translucent layer has a lower gas permeability with respect to the reducing gas compared to a gas permeability of the gas detection layer, the gas detection layer has a thickness of 10 μm to 100 μm.

These and other embodiments are described in greater detail below.

DESCRIPTION OF EMBODIMENTS

Figure 1:
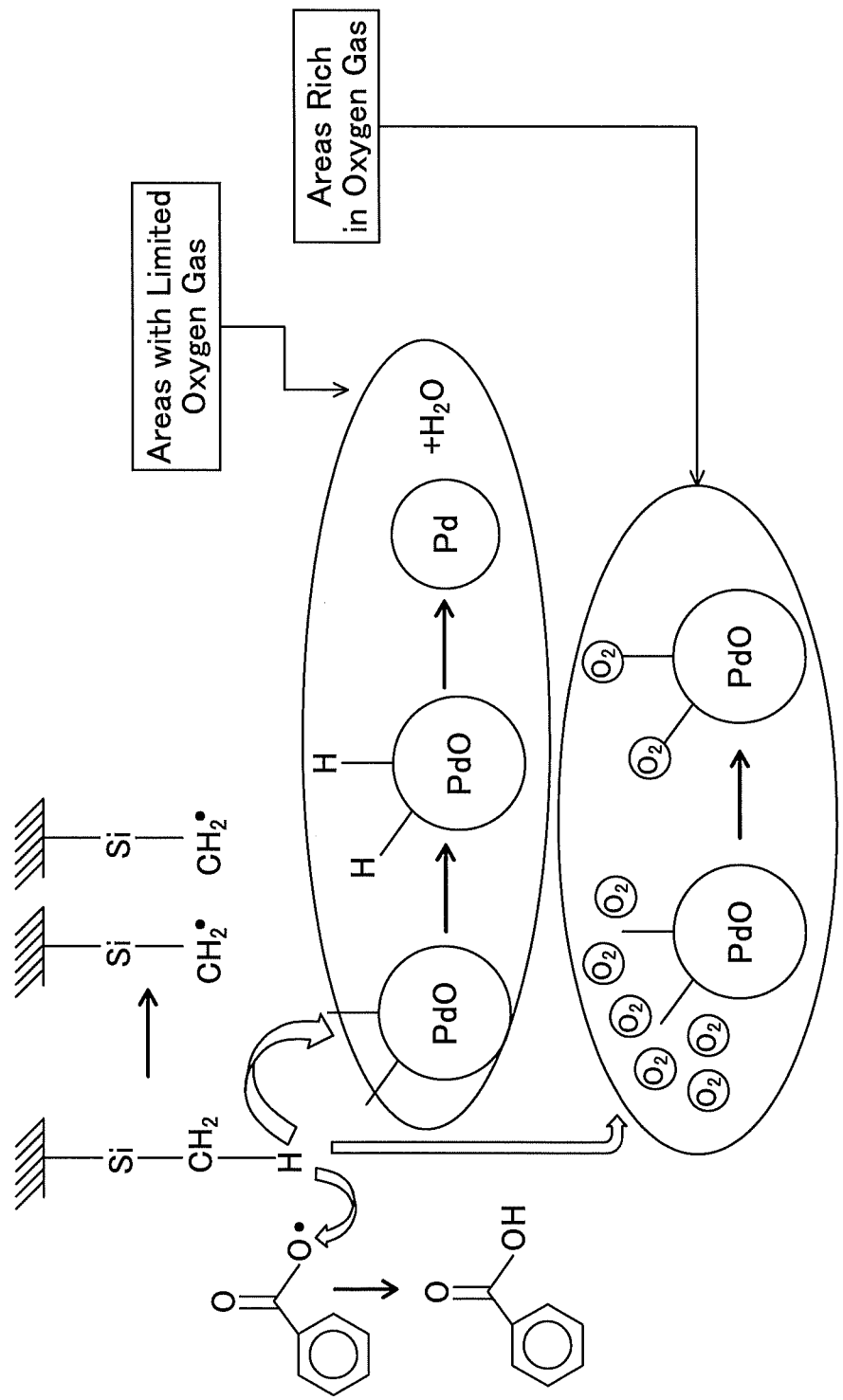
FIG. 1 is a depiction of one possible mechanism for a premature pigment color change as a result of crosslinking.
Figure 2:
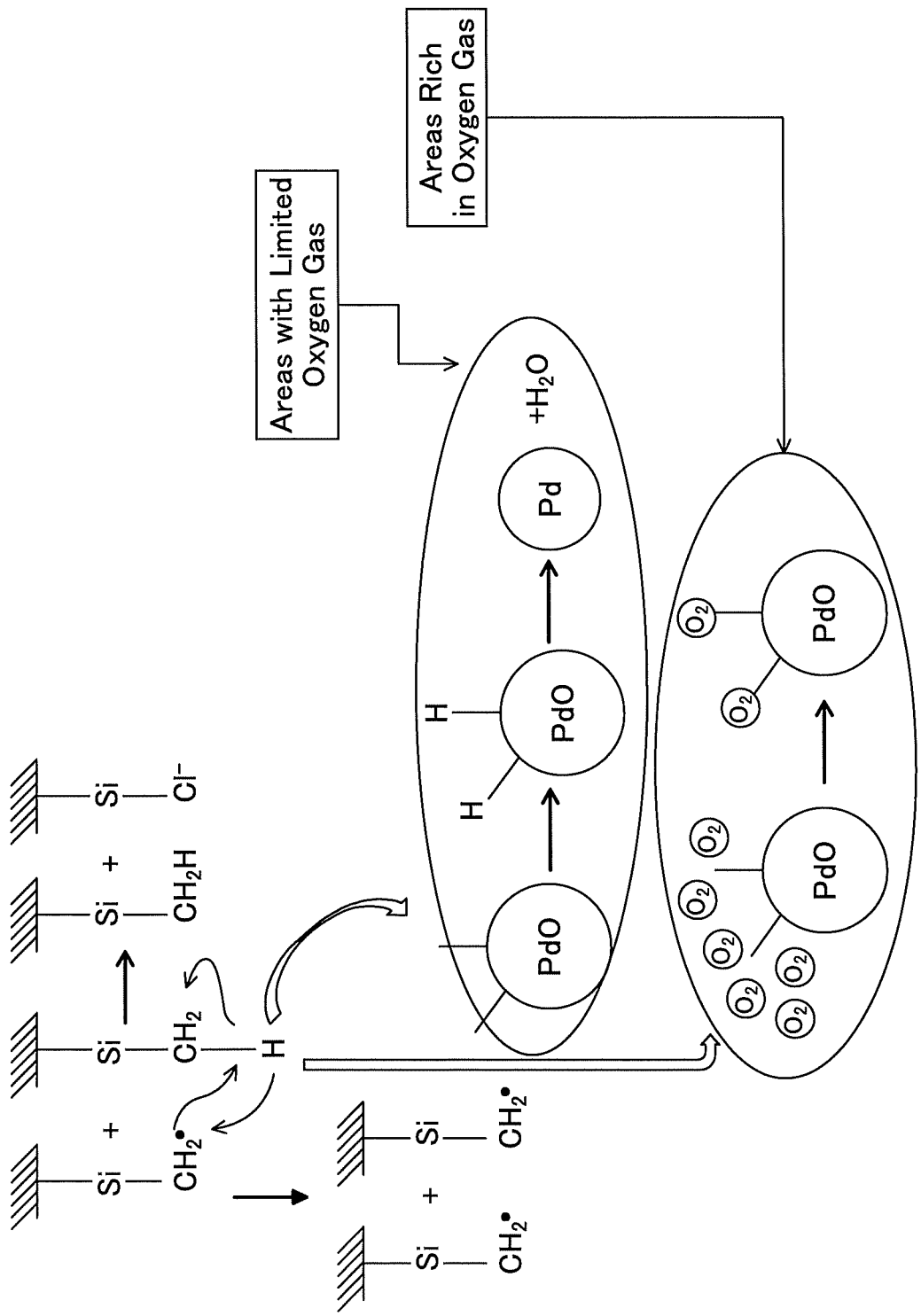
FIG. 2 is a depiction of another possible mechanism for premature pigment color change as a result of crosslinking.

It was confirmed that the presence of oxygen, which is present in the atmosphere or that which is artificially applied, which can penetrate the pressure sensitive adhesive layer, can cover the surface of the chemochromic reagent, thereby preventing the adsorption of low concentration/residual hydrogen and/or hydrogen molecules onto the detection compound. For example, if the detection compound formula is PdO, then oxygen present in the tape or in the atmosphere would prevent the reduction of PdO to Pd. While not wanting to be limited by theory, it is thought that the presence of oxygen would prevent adsorption of hydrogen on the PdO surface by either elimination of the radicals and/or blocking the active sites. It is thought that there are at least two possible mechanisms for the color change; each is detailed in FIG. 1 and FIG. 2. Increasing the presence of oxygen in the gas detection elements can be done by formulating specific embodiments of elements and/or by following specific methods for fabricating the aforementioned elements.

I. Pressure Sensitive Adhesive Gas Detection Element

Figure 3:
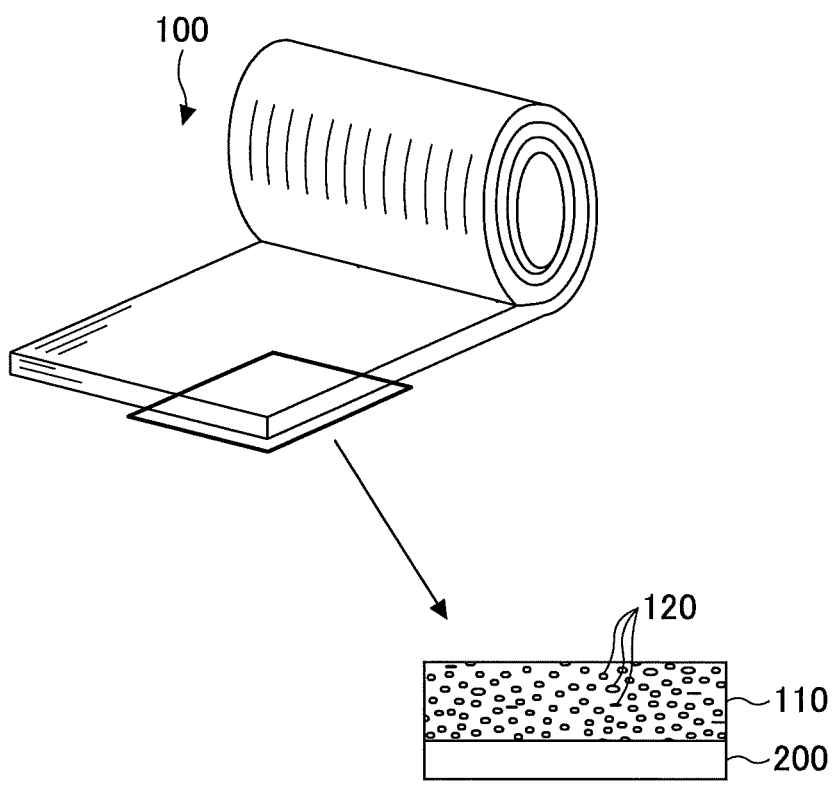
FIG. 3 is an illustration of a possible embodiment of a gas detection element.

In one embodiment, a gas detection element is described. In some embodiments, the gas detection element can detect the presence of reducing gases. In some embodiments, reducing gases detected can include hydrogen gas. In some embodiments, the gas detection element can comprise a pressure sensitive adhesive, or a pressure sensitive adhesive gas detection element. In some embodiments, as shown in FIG. 3, a gas detection element 100 can comprise a chemochromic composition 120 dispersed within a polymer matrix of a siloxane 110 (also referred to as "gas detection layer" herein) crosslinked by free radical transfer reaction with a peroxide initiator. In some elements, the resulting polymer matrix before use has a localized relative hydrogen gas presence (e.g., partial pressure) of less than the chemochromic activation threshold. In some embodiments, the resulting polymer matrix can be a pressure sensitive adhesive. In some embodiments, the element can further comprise a backing 200.

The gas detection layer may include a pressure sensitive adhesive.

Furthermore, the gas detection layer may include an adhesive selected from an acrylic pressure sensitive adhesive, a silicone-based pressure sensitive adhesive, a urethane-based pressure sensitive adhesive, and a rubber-based pressure sensitive adhesive.

The PSA disclosed herein may comprise, as its base polymer, one, two or more species among acrylic polymers, rubber-based polymers, polyester-based polymers, urethane-based polymers, and silicone-based polymers.

As the acrylic polymer, for example, a polymer of a monomeric starting material comprising an alkyl (meth) acrylate as a primary monomer and possibly comprising a secondary monomer copolymerizable with the primary monomer is preferable. The primary monomer herein refers to a component that accounts for higher than 50% by weight of the monomer composition in the monomeric starting material.

The rubber-based PSA refers to a PSA comprising a rubber-based polymer as a base polymer. Examples of rubber-based polymers comprise natural rubbers, styrene-butadiene rubbers (SBR), acrylonitrile-butadiene rubbers (NBR), isoprene rubbers, chloroprene rubbers, poly-isobutyle, butyl rubbers, reclaimed rubbers and the like. These can be used singly as one species or in combination of two or more species.

In some embodiments the chemochromic activation threshold can be qualitatively be determined as the color change which indicates the presence of a reducing gas, such as hydrogen, hydrogen sulfide, carbon monoxide, methane, formaldehyde, acetylene, sulfur dioxide, ammonia, and nitrous oxide.

In one embodiment, the gas sensing element may further include a release liner. The release liner is provided on the side opposite to the backing of the gas sensing element.

As the release liner, conventional release paper, etc., may be used, but the release liner is not particularly limited. For example, it is possible to use a release liner having a release treatment layer on the surface of the liner substrate such as a plastic film or paper, etc., or a release liner made of a low adhesive material such as a fluorine-based polymer (polytetrafluoroethylene, etc.) or a polyolefin resin, etc. As the plastic film, a substrate made of polyethylene terephthalate (PET), polypropylene (PP), or polyethylene (PE) is preferable. The aforementioned release-treated layer may be formed by surface-treating the aforementioned liner substrate with various release treatment agents such as those that are silicone-based, long-chain alkyl-based, fluorine-based, and molybdenum sulfide, etc. When the adhesive layer is a silicone-based adhesive, a fluorosilicone-based release treatment agent is preferable, and in the case of an acrylic-based adhesive, a silicone-based release treatment agent is preferable. The thickness of the release liner is not particularly limited; however, from the viewpoint of workability, approximately less than or equal to 3 mil and greater than or equal to 0.5 mil is appropriate. The thickness of the release treating agent is not particularly limited; an appropriate thickness is 0.1 µm to 1 µm.

A. Chemochromic Composition

In some embodiments, the gas detection element can comprise a chemochromic composition. In some embodiments, the chemochromic composition can comprise one or more chemochromic elements. In some embodiments, the chemochromic composition can define a plurality of chemochromic elements, such as a powder. In some embodiments, the chemochromic composition can further comprise a chemochromic dispersant. In some embodiments, the chemochromic elements can comprise a chemochromic reagent, or pigment, that can change color as a function of concentration of at least one target gas, e.g. hydrogen gas.

The gas detection layer can include a chemochromic composition. The chemochromic composition is preferably dispersed in the gas detection layer. In this case, the gas detection performance can be exerted more preferably.

In some embodiments, the chemochromic reagent can be an irreversible sensor, changing color irreversibly in the presence of the target gas. In some embodiments, the chemochromic reagent can comprise a detection compound. In some embodiments, the chemochromic reagent can comprise a noble metal. In some embodiments, the chemochromic element can also comprise a support. In some embodiments, the detection compounds and/or noble metal can be loaded on the support. In some embodiments, the materials loaded on the support can be bonded to the support by covalent bonding, ionic bonding, metallic bonding and/or Van der Waals forces. In some embodiments, the materials loaded on the support can be bonded to the support by strong Van der Waals forces.

In some embodiments, the support can comprise a metal oxide, a metal salt, or a mixed metal. In some embodiments, the metal oxide can comprise a transition metal oxide. In some embodiments, the transition metal oxide can comprise $Al_2O_3$, $SiO_2$, $ZrO_2$, $TiO_2$, $SrTiO_3$, $AlTiO_3$, or $SrZrO_3$. In some embodiments, the transition metal oxide can comprise $TiO_2$. In some embodiments, the metal salt can comprise an alkaline earth metal salt. In some embodiments, the metal in the alkaline earth metal salt can be selected from beryllium, magnesium, calcium, strontium, barium, or radium. In some embodiments, the alkaline earth metal salt can be $BaSO_4$. In some embodiments, the alkaline earth metal salt can be $CaCO_3$. While not wanting to be limited by theory, it is thought that using divalent support material other than titania such as $BaSO_4$ or $CaCO_3$ can improve oxidation kinetics and detection sensitivity. In some embodiments, the support can comprise a mixture of a transition metal and an alkaline earth metal (e.g. $TiO_2$ and $BaSO_4$; $TiO_2$ and $CaCO_3$; and $TiO_2$, $BaSO_4$, and $CaCO_3$). While not wanting to be limited by theory, the material for the support is generally selected so that interaction of the metal particles with the surface of support surface reduces the total energy required for reduction of the detection compound so that the sensitivity of the detection compound can be increased. Such an interaction suggests a small chemical interaction between support and the metal particles allowing for the destabilization of the detection compound particles on the surface of the support by the presence of a second metal (e.g., platinum lowers the activation energy required for palladium oxide reduction). In some embodiments, the support can comprise particles having a size in a range from about 0.1 µm to about 15 µm. In some embodiments, the support particle size can range from about 0.2 µm to about 10 µm for pigment applications to maximize opacity once reacted with the target gas.

In some embodiments, the chemochromic reagent can comprise a noble metal group loaded with the detection compound on the support. In some embodiments, the detection compound can comprise a palladium based compound. In some embodiments, the palladium based compound can comprise palladium oxide, palladium hydroxide, or a palladium salt. In some embodiments, the detection compound can comprise palladium oxide. In some embodiments, the detection compound can comprise palladium hydroxide. In some embodiments, the detection compound can comprise palladium salt. In some embodiments, the detection compound can have a median size in the range of about 2 nm to about 30 nm, or about 5 nm to about 25 nm. In some embodiments, the relative weight ratio of the detection compound to the support can range from about 1:9, about 1:20, about 1:30 to about 1:200, about 1:300, or any combination thereof. In some embodiments, the relative weight ratio of the detection compound to the support can range from about 1:20 to about 1:190. In some embodiments, the mass ratio of detection compound to support can range from about 0.1 wt % to about 10 wt %. In some embodiments, the mass ratio of the detection compound to the support can range from about 0.25 wt % to about 7.5 wt %. In some embodiments, the mass ratio of the detection compound to the support can range from about 0.5 wt % to about 3.5 wt %.

In some embodiments, the chemochromic composition may be in the form of a pigment. The pigment may include carrier particles and palladium oxide supported on the surfaces of the carrier particles. Furthermore, a noble metal other than palladium may be supported or loaded on the surfaces of the carrier particles. Furthermore, the carrier particles may be titanium dioxide. In some embodiments, the noble metal material can comprise a metal, salt, or an oxide of a noble metal. In some embodiments, the noble metal material can comprise at least a metal, salt, or an oxide of a noble metal other than palladium. In some embodiments, the noble metal material can comprise gold, silver, or platinum group metals, such as platinum, iridium, osmium, rhodium, or ruthenium. In some embodiments, the noble metal material can comprise platinum. While not wanting to be limited by theory, it is thought that a palladium based oxidation catalyst such as PdO when mixed with non-palladium particles comprising a noble metal or noble metal compounds can provide an oxidation catalyst which oxidizes a reducing gas with significantly sped up oxidation kinetics and significantly increased sensitivity as compared to an oxidation catalyst of palladium (e.g., PdO) alone. In some embodiments, the noble metal material can have a median size in the range from about 2 nm to about 10 nm. In some embodiments, the mass ratio of the noble metal material to the support-with-detection compound can range from about 0.01 wt %, about 0.03 wt %, about 0.05 wt %, about 0.07 wt %, about 0.075 wt %, about 0.1 wt %, about 0.2 wt %, about 0.3 wt %, about 0.4 wt %, to about 0.5 wt %, about 0.6 wt %, about 0.7 wt %, about 0.8 wt %, about 0.9 wt %, about 1.0 wt %, or any combination thereof.

In some embodiments, the chemochromic composition can comprise between about 0.1 wt % to about 25 wt % of the total mixture before curing. The weight percentage does not include the weight of any optional backing.

In some embodiments, the chemochromic composition can comprise particles having an average size of less than 20 µm, less than 15 µm, less than 10 µm, less than 5 µm, less than 0.5 µm, or less than 0.1 µm. In some embodiments, the chemochromic composition can comprise particles having an average size of less than 10 µm.

B. Polymerized Siloxane Matrix

For some elements, the siloxane polymer matrix can be formed by curing of one or more siloxane precursors. In some embodiments, the siloxane precursors can comprise an organosiloxane. In some embodiments, the siloxane precursors can additionally comprise an oligosiloxane. In some embodiments, curing can be by crosslinking the siloxane precursors. In some embodiments, the crosslinking can be done by way of free radical transfer reaction with a treatment liquid. In some embodiments, the treatment liquid can comprise an initiator.

In some embodiments, the organosiloxane can be one or more methyl siloxanes. In some embodiments, the methyl siloxane can comprise a polymer or a monomer. In some embodiments, the methyl siloxane can comprise a polymer. In some embodiments, the methyl siloxane polymers can be linear or cyclic. Some polymer methyl siloxanes can comprise a linear polydimethyldisiloxane or a cyclic polydimethylsiloxane, such as a polydimethyl disiloxane. Some polymer methyl siloxanes can comprise a linear polymethylphenylsiloxane or a cyclic polymethylphenylsiloxane. In some embodiments, the cyclic methyl siloxane polymers can comprise the cyclomethicones such as: hexamethylcyclotrisiloxane, octamethylcyclotetrasiloxane, decamethylcyclo-pentasiloxane, dodecamethylcyclohexasiloxane, or combinations thereof. In some embodiments, the linear polymer methyl siloxanes can comprise the linear siloxanes such as: hexamethyldisiloxane, octamethyltrisiloxane, decamethyltetrasiloxane, dodecamethylpentasiloxane, tetradecamethylhexasiloxane, or combinations thereof. In some embodiments, the organosiloxane can comprise octamethylcyclotetrasiloxane, decamethylcyclopentasiloxane, or combinations thereof. In some embodiments, a suitable example of a polydimethylsiloxane is sold under the brand name of DOW CORNING® 282 ADHESIVE. In some embodiments, a suitable example of a polymethylphenylsiloxane is sold under the brand name of SilGrip*® PSA518, Momentive.

In some embodiments, the oligosiloxane can comprise a silicone resin. While not wanting to be limited by theory, it is thought that the silicone resin to the siloxane precursors can add tackiness to the resulting pressure sensitive adhesive. In some embodiments, the silicone resin can comprise an oligosiloxane with $Me_3SiO$ and $SiO_4$ terminal units such as an MQ resin.

In some embodiments, the treatment liquid can comprise an initiator. In some embodiments, the initiator can comprise a peroxide. Some initiators can comprise a peroxide selected from benzoyl peroxide or 2,4-dichlorobenzoyl peroxide. In some embodiments, the initiator can be a free radical initiator that initiates crosslinking between the siloxane precursor moieties. In some embodiments, the activation of the free radical initiator can result in the initiator not forming part of the covalent linkage between the moieties. In other embodiments, the activation of the free radical initiator can result in the initiator forming part of the covalent linkage between the moieties. In some embodiments, the initiator can comprise between about 0.1 wt % to about 5.0 wt % based on the weight of the siloxane precursor (silicon solids).

In some embodiments, the treatment liquid can further comprise plasticizers, which include type 1 plasticizers that can generally decrease the glass transition temperature (Tg), e.g. makes it more flexible, phthalates (n-butyl, dibutyl, dioctyl, butyl benzyl, missed esters, and dimethyl); and type 2 plasticizers that can enable more flexible, more deformable layers, and perhaps reduce the amount of voids resulting from lamination, e.g., glycols (polyethylene; polyalkylene; polypropylene; triethylene; dipropylglycol benzoate).

Type 1 plasticizers can include, but are not limited to: butyl benzyl phthalate, dicarboxylic/tricarboxylic ester-based plasticizers such as but not limited to phthalate-based plasticizers such as but not limited to bis(2-ethylhexyl) phthalate, diisononyl phthalate, bis(n-butyl)phthalate, butyl benzyl phthalate, diisodecyl phthalate, di-n-octyl phthalate, diisooctyl phthalate, diethyl phthalate, diisobutyl phthalate, di-n-hexyl phthalate and mixtures thereof; adipate-based plasticizers such as but not limited to bis(2-ethylhexyl) adipate, dimethyl adipate, monomethyl adipate, dioctyl adipate and mixtures thereof; sebacate-based plasticizers such as but not limited to dibutyl sebacate, and maleate.

Type 2 plasticizers can include, but are not limited to: dibutyl maleate, diisobutyl maleate and mixtures thereof, polyalkylene glycols such as but not limited to polyethylene glycol, polypropylene glycol and mixtures thereof. Other plasticizers which may be used include but are not limited to benzoates, epoxidized vegetable oils, sulfonamides such as but not limited to N-ethyl toluene sulfonamide, N-(2-hydroxypropyl)benzene sulfonamide, N-(n-butyl)benzene sulfonamide, organophosphates such as but not limited to tricresyl phosphate, tributyl phosphate, glycols/polyethers such as but not limited to triethylene glycol dihexanoate, tetraethylene glycol diheptanoate and mixtures thereof; alkyl citrates such as but not limited to triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, alkyl sulphonic acid phenyl ester, and mixtures thereof.

In some embodiments, the treatment liquid can further comprise a solvent. In some embodiments, the solvent can comprise one or more compositions that result in a solution of siloxane precursor and initiator that is substantially blended when the siloxane precursor and the initiator are dissolved in the solvent and stirred.

Backing

In some embodiments, as shown in FIG. 3, the pressure sensitive adhesive gas detection element can further comprise a backing 200 (also referred to as "backing layer" herein). For some elements, the chemochromic-composition containing polymeric matrix is coated onto the backing as a layer, to form a tape. In some embodiments, the backing can be permeable to oxygen or air. In some embodiments, the backing can comprise a plant-based composition, such as cellulose, paper, cardboard, etc. In some embodiments, the backing can be a polymer-based backing. In some embodiments, the backing can comprise polyimide, polypropylene (PP), fluorinated ethylene propylene (FEP), ethylene tetrafluoroethylene (ETFE), polyethylene (PE), polytetrafluoroethylene (PTFE), perfluoroalkoxy alkanes (PFA), or polyethylene terephthalate (PET).

In some embodiments, the backing can be resistant to ultraviolet (UV) radiation. In some embodiments, the backing can further comprise an UV stabilization compound to remedy possible adverse environmental effects. In some embodiments, the UV stabilization compound can be present in the polymer matrix. In some embodiments, the UV stabilization compound can be present in both the backing and the polymer matrix. In some embodiments, the UV stabilization compound can comprise a UV absorber, a UV blocker, a hindered amine light stabilizer (HALS), or a mixture thereof. The UV blocker can comprise $ZnO_2$ or $TiO_2$. The UV absorber can comprise compounds from the triazine family, such as benzotriazol or a benzopheneone. The HALS can comprise a high molecular weight HALS (MW>1000 g/mol) or low molecular weight HALS (MW≤1000). The UV ultraviolet (UV) stabilization compound can be in the range of about 0.1 wt % to about 10 wt % as compared to the total mass of the backing.

C. Primer

Some embodiments of elements can also comprise a primer. In some embodiments, the primer can be in physical communication with the backing and the pressure sensitive adhesive matrix. While not wanting to be limited by theory, a primer can be adopted to improve the way for the pressure sensitive adhesive to "stick out" at time of cutting. In some embodiments, the primer can be compatible with the pressure sensitive adhesive matrix. In some embodiments, the primer can be compatible with phenyl-type silicone. The thickness of the primer is not particularly limited; for example, the thickness is in a range of 0.1 μm to 5 μm, and preferably in a range of 0.1 μm to 2 μm.

Here, referring back to FIG. 3, this gas detection element 100 has a feature in that the polymer matrix layer 110 of siloxane (hereinafter referred to as "gas detection layer") has sufficient adhesion.

More specifically, the gas detection layer 110 has an adhesion of greater than or equal to 0.2 N/25 mm. The adhesion is preferably greater than or equal to 1.0 N/25 mm, greater than or equal to 1.5 N/25 mm, greater than or equal to 2.0 N/25 mm, greater than or equal to 3.0 N/25 mm, or greater than or equal to 5.0 N/25 mm. The gas detection layer 110 preferably has adhesion of less than or equal to 10.0 N/25 mm.

Note that in the present embodiment, the adhesion is measured by a 180° peel strength test.

When the gas detection element 100 having the above feature is used, the gas detection layer 110 can be used as an adhesive layer. That is, by pressing the gas detection layer 110 against the measurement target, the gas detection element 100 can be adhered to the measurement target.

While not wanting to be limited by theory, it is thought that the adhesive layer can provide sufficient tack and mechanical strength to a measurement target such that when pressed against said target it can resist detachment forces and remain attached to the target.

In this case, there is no need to use, for example, an adhesive tape as a separate auxiliary tape, in order to fix the gas detection layer to the measurement target as in the conventional technology, and therefore the work efficiency can be increased. Particularly, the gas detection element 100 can be adhered to the measurement target by its own adhesion. Therefore, there is no need to use a separate fixing means.

Furthermore, in the gas detection element 100, the gas detection layer 110 can also function as an adhesive layer. Therefore, it is possible to significantly reduce problems which may occur in the conventional gas detection tape due to separately providing an adhesive layer, such as the structure becoming complicated and the measurement precision being reduced. For example, even when there is a hole in the surface of the measurement target, or when the measurement target is not planar, the gas detection layer can be appropriately fixed to the measurement target without coming off.

In this way, by way of the gas detection element 100, compared to the conventional technology, the workability of the worker can be improved when using the gas detection element 100, and additionally, it is possible to significantly reduce problems such as the structure becoming complicated and the measurement precision being reduced.

Note that in the gas detection element 100, the gas detection layer 110 may have an adhesion property with respect to the second surface of the backing 200 (in FIG. 3, the surface of the backing 200 opposite to the surface on which the gas detection layer 110 is disposed (the first surface)).

Furthermore, on the first surface or the second surface of the backing, "markings" such as a grid, scale marks, and arrows, etc., may be arranged. When the markings are a grid, the user can refer to the grid to quantitatively recognize an area where the color has changed, when the color of the gas detection element 100 changes. The grid may be a lattice in the longitudinal and transverse directions, or may be in other shapes.

The method of arranging the markings is not particularly limited. The markings may be arranged on the first surface or the second surface of the backing, for example, by printing.

The gas detection element according to an embodiment of the present invention can have the following features:

(i) Chemochromic pigment particles included in the gas detection layer that indicate an irreversible color-change reaction when exposed to reducing gas.

(ii) On a first surface of the gas detection layer, a translucent layer is disposed, and the translucent layer has a lower gas permeability with respect to the reducing gas, compared to the gas detection layer.

(iii) The gas detection layer has a thickness of 10 μm to 100 μm.

Note that in the present application, the "reducing gas" includes at least one of hydrogen, hydrogen sulfide, carbon monoxide, methane, formaldehyde, acetylene, sulfur dioxide, ammonia, and nitrous oxide.

The features are respectively described in detail as follows.

In the gas detection element according to an embodiment of the present invention, according to the feature of (i), once the gas detection layer contacts the reducing gas (hereinafter, also referred to as "detection gas") and the color changes, the changed color of the gas detection layer can be maintained thereafter (so-called irreversible or permanent color-change).

That is, in a case where the chemochromic pigment particles indicate a reversible reaction with respect to the detection gas, when the detection gas is no longer present around the chemochromic pigment particles, the color of chemochromic pigment particles reverses back to the original color (so-called fading phenomenon).

Therefore, in a case of reversible reaction in order to maintain the changed color, the detection gas needs to be continuously flowing and in contact with the chemochromic pigment particles. If the flow of detection gas is stopped prior to inspection, the color-change fades and hence the indicator to the location of the detection gas leak is lost. Furthermore, in a situation where there is only a small amount of detection gas, it is difficult to maintain the changed color of the gas detection layer.

On the other hand, in the gas detection element according to an embodiment of the present invention, once the chemochromic pigment particles contact the detection gas and a color reaction occurs, the changed state is maintained thereafter. Therefore, even if a small amount of detection gas contacts the chemochromic pigment particles, the changed color can be maintained. Note that the term "irreversible" is a concept including a mode where the color changes permanently, and also an impermanent mode, that is, a mode in which a state where the color has substantially changed is maintained over a desired period of time (for example, one month).

Furthermore, the gas detection element according to an embodiment of the present invention is able to perform the measurement using a wide area of the gas detection layer, according to the feature of (ii).

That is, in the gas detection element according to an embodiment of the present invention, on a first surface of the gas detection layer, a translucent layer is disposed, and the translucent layer has a lower permeability with respect to the detection gas, compared to the gas detection layer. Therefore, the detection gas, which has entered from the second surface of the gas detection layer, can be "trapped" in the gas detection layer.

Furthermore, according to the above, even more chemochromic pigment particles included in the gas detection layer can be used for the color reaction. As a result, even more distinct color changes can be expressed.

Furthermore, the translucent layer has a lower gas permeability with respect to the measurement target gas, compared to the gas detection layer. For example, the translucent layer may have a gas permeability that is less than or equal to $1/10$ of that of the gas detection layer.

The translucent layer preferably has flexibility.

The translucent layer may be formed of, for example, polyimide, polyethylene, fluorinated ethylene propylene copolymer (FEP), or ethylene tetrafluoroethylene copolymer (ETFE), etc.

Note that the "translucent layer" is not necessarily limited to the shape of a "layer". The "translucent layer" may be in a shape of a film, a sheet, or a plate.

Furthermore, by the gas detection element according to an embodiment of the present invention, it is possible to clearly recognize whether a color reaction has occurred, according to the feature of (iii).

That is, in an embodiment where the gas detection layer is relatively thin, and the translucent layer has a translucency as described above, even when a color reaction occurs near the second surface of the gas detection layer (i.e., the surface opposite to the surface on which the translucent layer is set) of the gas detection layer, it is possible to easily recognize the change in the color from the side of the translucent layer, that is, from the outside. Furthermore, it is possible to express the color change relatively quickly, across the entire thickness direction of the gas detection layer.

The thickness of the gas detection layer is preferably more than 5 µm, more than 10 µm, or more than 30 µm. The thickness of the gas detection layer is preferably less than 200 µm, less than 100 µm, or less than 80 µm. The thickness of the gas detection layer is preferably between 5 µm and 80 µm. Note that if the thickness is less than 5 µm, the concentration per area of the chemochromic pigment particles decreases, and the color change may not sufficiently occur in the gas detection layer.

Note that the concentration of the chemochromic pigment particles included in the gas detection layer is preferably in a range of 1 wt % to 20 wt % with respect to the entire gas detection layer, more preferably in a range of 5 wt % to 10 wt % with respect to the entire gas detection layer.

The color change ($\Delta L^*$) may be greater than or equal to 5, at least in the part that directly contacts the gas. The color change ($\Delta L^*$) is preferably greater than or equal to 10, at least in the part that directly contacts the gas.

Note that the color change ($\Delta L^*$) can be evaluated by the following method.

By using a colorimeter, the chromaticity of a standard whiteboard is measured. Furthermore, the chromaticity before using the gas detection element is measured. Note that the chromaticity is expressed by the lightness index of the L*a*b* color system (CIELAB1976). The absolute value of the difference in the measured chromaticity between the standard whiteboard and the gas detection element before being used is obtained as $L^*_{initial}$.

Similarly, the chromaticity after using the gas detection element is measured. The absolute value of the difference in the measured chromaticity between the standard whiteboard and the gas detection element after being used is obtained as $L^*_{final}$.

From the above results, the color change ($\Delta L^*$) of the gas detection element can be evaluated by $\Delta L^* = |L^*_{final} - L^*_{initial}|$.

II. Method for Producing a Pressure Sensitive Gas Detection Adhesive.

Figure 4:
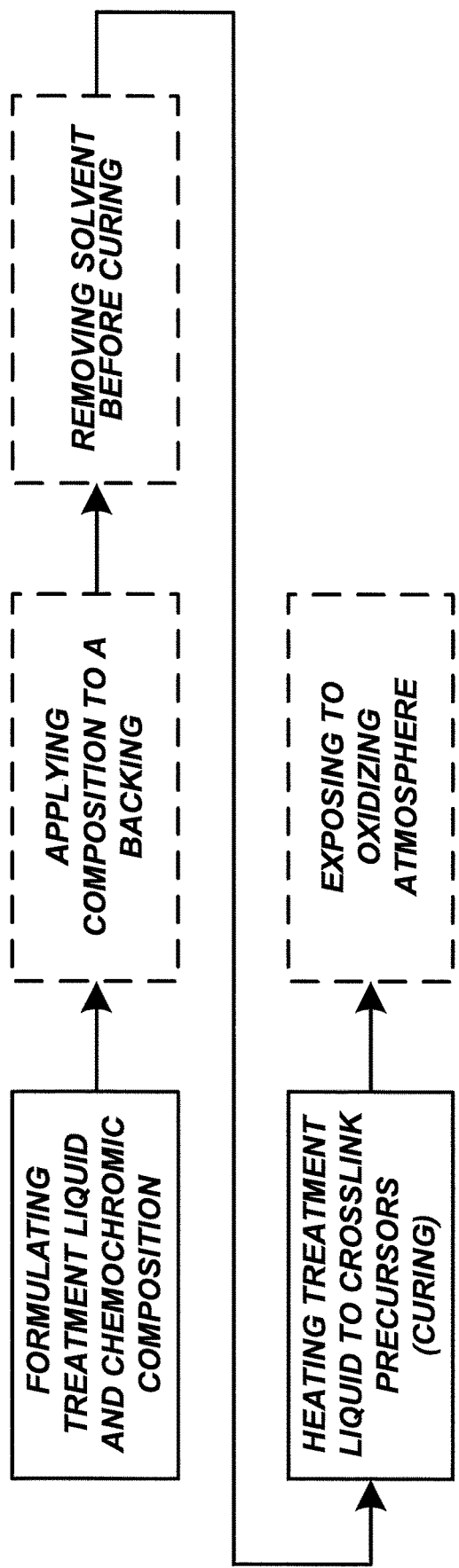
FIG. 4 is a depiction of one possible methodology for fabricating a gas detection element.

A method of producing a pressure sensitive gas detection adhesive can be described, such as the one shown in FIG. 4. The method may comprise: (1) formulating a treatment liquid and a chemochromic composition, the treatment liquid comprising a siloxane precursor and an initiator; and (2) heating the treatment liquid to a temperature sufficient to activate the initiator so that the precursor is crosslinked to create a polymer matrix containing the chemochromic composition, where the polymer matrix can have a localized hydrogen gas presence less than the threshold for activating the chemochromic composition. In some embodiments, the resulting polymer matrix can be a pressure sensitive adhesive.

For some methods, formulating a treatment liquid and a chemochromic composition can comprise mixing the treatment liquid and the chemochromic composition.

In some embodiments, the chemochromic composition can comprise one or more chemochromic elements. In some embodiments the chemochromic composition can define a plurality of chemochromic elements, such as a powder. In some embodiments, the chemochromic elements are the same aforedescribed elements. In some chemochromic compositions, the chemochromic composition can further comprise a dispersant for the chemochromic elements. In some embodiments, the dispersant can comprise methyl ethyl ketone. In some embodiments, the chemochromic composition can comprise between about 0.1 wt % to about 25 wt % of the total mixture before curing. The weight percentage does not include the weight of any optional backing. In some embodiments, the chemochromic composition can comprise about 1 wt %, about 3 wt %, about 5 wt % about 10 wt %, about 10.8 wt %, about 11.1 wt %, or about 15.0 wt % of the total mixture before curing.

In some embodiments, the siloxane polymer matrix can be formed by curing, or crosslinking, of one or more siloxane precursors. In some embodiments, the treatment liquid can comprise a siloxane precursor and an initiator. In some embodiments, the siloxane precursors can comprise an organosiloxane. In some embodiments, the siloxane precursors can additionally comprise an oligosiloxane. In some embodiments, curing can be by crosslinking the siloxane precursors. In some embodiments, the crosslinking can be done by way of free radical transfer reaction within the treatment liquid.

In some embodiments, the organosiloxane can be one or more methyl siloxanes. In some embodiments, the methyl siloxane can comprise a polymer or a monomer. In some embodiments, the methyl siloxane can comprise a polymer. In some embodiments, the methyl siloxane polymers can be linear or cyclic. Some polymer methyl siloxanes can comprise a linear polydimethyldisiloxane or a cyclic polydimethylsiloxane. Some polymer methyl siloxanes can comprise a linear polymethylphenylsiloxane or a cyclic polymethylphenylsiloxane. In some embodiments, the cyclic polymer methyl siloxanes can comprise a cyclomethicone such as: hexamethylcyclotrisiloxane, octamethylcyclotetrasiloxane, decamethylcyclopenta-siloxane, dodecamethylcyclohexasiloxane, or combinations thereof. In some embodiments, the linear polymer methyl siloxanes can comprise a linear siloxane such as: hexamethyldisiloxane, octamethyltrisiloxane, decamethyltetrasiloxane, dodecamethylpentasiloxane, tetradecamethylhexasiloxane, or combinations thereof. In some embodiments, the siloxane precursor can comprise octamethylcyclotetrasiloxane, decamethylcyclopentasiloxane, or combinations thereof.

In some embodiments, the oligosiloxane can comprise a silicone resin. While not wanting to be limited by theory, it is thought that the silicone resin to the siloxane precursors can add tackiness to the resulting pressure sensitive adhesive. In some embodiments, the silicone resin can comprise an oligosiloxane with $Me_3SiO$ and $SiO_4$ terminal units such as an MQ resin.

For some methods, the initiator can comprise a peroxide. In some embodiments, the initiator can comprise an initiator selected from benzoyl peroxide or 2,4-dichlorobenzoyl peroxide. In some embodiments, the initiator can comprise between about 0.1 wt % to about 5.0 wt % based on the weight of the siloxane precursor (silicon solids).

In some embodiments, the treatment liquid can further comprise a solvent. In some embodiments, the solvent can comprise one or more compositions that result in a solution of siloxane precursor and initiator that is substantially blended when the siloxane precursor and the initiator are dissolved in the solvent and stirred. In some embodiments, the solvent can comprise an alkylbenzene such as: methyl benzene, ethyl benzene, etc. In some embodiments, the methyl benzene can be selected from xylene or toluene. In some embodiments, xylene can comprise 1,2-dimethylbenzene (o-xylene), 1,3-dimethylbenzene (m-xylene), 1,4-dimethylbenzene (p-xylene), or any combination thereof.

In some embodiments, the heating step can further comprise the additional step of removing any solvent from the treatment liquid before heating the treatment liquid to activate the initiator. In some embodiments, to remove the solvent from the treatment liquid, the liquid can be heated at a temperature range from about 25° C. to 100° C. For example, in the case of 25° C., the heating time is preferably approximately 10 minutes, and in the case of 100° C., the heating time is preferably approximately 30 seconds.

In some embodiments, heating the treatment liquid to a temperature sufficient to activate the initiator can comprise heating to a temperature sufficient for curing, or analogously for the initiator to cause crosslinking between the siloxane precursor moieties. In some embodiments, heating to a temperature sufficient to activate the initiator can comprise heating the treatment liquid at a temperature from 120° C. to 200° C., for 1 to 3 minutes.

In some methods, there can be the additional step of applying the formulated liquid and chemochromic composition on a backing. In some embodiments, the applying the formulated treatment liquid and chemochromic composition can be in the form of a layer to form a tape. In some embodiments, applying the formulated treatment liquid and chemochromic composition is done before heating.

In some embodiments, the backing can be a polymeric backing. In some embodiments, the backing can be a polymer-based backing. In some embodiments, the polymer-based backing can comprise polyimide, fluorinated ethylene propylene (FEP), ethylene tetrafluoroethylene (ETFE), polyethylene (PE), polytetrafluoroethylene (PTFE), perfluoroalkoxy alkanes (PFA), or polyethylene terephthalate (PET). In some embodiments, the backing can be resistant to UV radiation.

In some embodiments, applying the contacted treatment liquid and chemochromic composition can be done by methods known by those skilled in the art for creating a layer of desired thickness, such as, by film coating, bar coating, blade coating, spray coating, dip coating, die coating, spin coating, etc. In some embodiments, the application is done by film coating. In some embodiments, the contacted treatment liquid and chemochromic composition can be coated to form a layer with a post-cure thickness of between about 5 µm to about 200 µm, or about 25 µm, 30 µm, 45 µm, 60 µm, or 85 µm.

For some methods, the method can further comprise the step of exposing the polymer matrix to an oxygen-containing atmosphere. While not wanting to be limited by theory, it is believed that the trace amounts of elemental hydrogen created during matrix crosslinking can be blocked from attaching to active sites in the chemochromic composition by the increased presence of elemental oxygen in the surrounding atmosphere, which in turn permeates the polymer matrix blocking the chemochromic reagent's active sites. In some embodiments, exposing oxygen-containing atmosphere can comprise an exposing to air. In some embodiments, exposing to an oxygen-containing atmosphere can comprise exposing to a gas with at least 10 vol % oxygen gas, at least 15 vol % oxygen gas, at least 20.95 vol % oxygen gas, at least 30 vol % oxygen gas, or at least 40 vol % oxygen gas. In some embodiments, the step of exposing the polymer matrix to an oxygen-containing atmosphere can comprise maintaining the physical dimensions of the pressure sensitive adhesive material to less than an amount sufficient to allow contact of the resulting pressure sensitive adhesive to the oxygen-containing atmosphere. In some embodiments, the step of exposing the polymer matrix to an oxygen-containing atmosphere can comprise a combination of backing material selection for permeability and maintaining the physical dimensions of the pressure sensitive adhesive material.

In some embodiments, exposing the polymer matrix to an oxygen-containing atmosphere can comprise using a release liner that may be permeable to an oxygen-containing atmosphere.

In some embodiments, using a release liner can comprise using a liner that is permeable to oxygen. In some steps, using a release liner may comprise using a liner that is permeable to air. In some embodiments, using a permeable release liner can comprise using a liner that can comprise a plant-based or plastic film which is permeable to air and/or oxygen, such as cellulose, paper, cardboard, polyethylene terephthalate (PET), polyethylene (PE), polypropylene (PP), etc.

In some embodiments, the backing can be a polymeric backing. In some embodiments, the backing can be a polymer-based backing. In some embodiments, the polymer-based backing can comprise polyimide (Nylon), fluorinated ethylene propylene (FEP), ethylene tetrafluoroethylene (ETFE), polyethylene (PE), polytetrafluoroethylene (PTFE), perfluoroalkoxy alkanes (PFA), or polyethylene terephthalate (PET). In some embodiments, the backing can be resistant to UV radiation.

EXAMPLES

Example 1.1: Compound/Mixture Formulation

Fabrication of the Chemochromic Elements (0.3 wt % Pt on a 3.0 wt % PdO/$TiO_2$ Support).

Depositing PdO on $TiO_2$:

To deposit PdO, a slurry of 2.5 g $TiO_2$ (<5 μm size, rutile, Sigma Aldrich) in 100 mL of DI water was adjusted to pH 10.6 using a NaOH solution (12M solution from pure pellets and DI water, EMD Millipore) and stirred at 70° C. for one hour. Then, 2.50 mL of $PdCl_2$ solution (0.281 M in 2 M HCl, Aldrich) was added dropwise to the mixture, taking care to keep the solution at pH 10.6 using a NaOH solution (12 M sol., EMD Millipore). Once all the $PdCl_2$ solution was added, the pH of the mixture was then adjusted to 8 using HCl (3 M, Aldrich). The mixture was then stirred and heated for one hour while the PdO was deposited onto the surfaces of the titania supports. The resulting solid PdO/$TiO_2$ particulates were then filtered, washed thoroughly with DI water and dried at 110° C. for 3 hours, to yield a solid, compound #1 (C-1) of 3.3 wt % PdO.

Pt Loading:

Then, to give a loading of about 0.3 wt % Pt on the support, 0.019 g $Na_2PtCl_6 \cdot 6H_2O$ (Aldrich) was added to a slurry of 2.5 g C-1 suspended in 100 mL of ethanol (Aldrich). The pH of the resulting solution was then adjusted to 6 using NaOH (12 M sol., EMD Millipore). Sonication was then carried out on the reaction mixture using a direct immersion titanium tip ultrasonic homogenizer set at 20 kHz, 100 W·$cm^{-2}$ (Omni-ruptor 4000, Omni International, Inc.) at room temperature. The resulting product was filtered, thoroughly washed with ethanol (Aldrich), and then dried at room temperature. Then, the product was baked at 110° C. for 3 hours to provide chemochromic elements of 0.26 wt % Pt, or CC-1.

Example 2.1: Element Formulation

Fabrication of Gas Detection Element #1.

Creating the Coating Mixture:

The treatment liquid was created by adding benzoyl peroxide (1.115 g, 97%, Luperox® A98, Aldrich) to toluene (10.0 g, Aldrich), stirring the resulting solution for 1 minute to fully dissolve the benzoyl peroxide. Then the resulting solution and toluene (16.92 g, Aldrich) were all added to pressure sensitive adhesive precursor (72.1 g, DOW CORNING® 282 ADHESIVE) and stirred by hand for 3 minutes to form a treatment liquid. A chemochromic composition was created by dispersing CC-1 (2.29 g) in methyl ethyl ketone (15 g, Aldrich) making sure to break up any large chunks to create a dispersion. The chemochromic composition was then added to the treatment liquid and mixed by hand until uniform, about 3 minutes. The result was a coating mixture.

Coating the Pressure Sensitive Adhesive on the Backing:

The resulting coating mixture was then film coated using bar applicator (SA-210, Baker-Type-Applicator, Tester Sangyo Co., Ltd.) on a 30 cm×40 cm polyimide backing (1 mil, 100 PST Kapton, Dupont High Performance Films) with the dial set to the desired pressure sensitive adhesive thickness. The coating mixture was placed in front of the applicator and the applicator was then pulled across the backing coating it as it progressed. The result was a coated backing.

Removing Solvent and Curing Pressure Sensitive Adhesive:

The coated backing was then air dried at 25° C. for 30 seconds to remove the solvent. Next, the coated backing was then cured in an oven at 177° C. for 3 minutes. The result was a pressure sensitive adhesive gas detection element (GDE-1).

Example 2.2: Element Formulation

Fabrication of Additional Gas Detection Elements.

Additional gas detection elements were synthesized using methods similar to those used in Example 2.1 with the exception of the changes outlined in Table 1. Additional materials used were: pressure sensitive adhesive (SilGrip*® PSA518, Momentive), fluorinated ethylene propylene (FEP) backing (2 mil, 200C FEP100/Teflon, Dupont High Performance Films, Circleville), polyethylene (PE) backing (1 mil, S1113, Uline), and polyethylene terephthalate (PET) (2 mil, PET/Lumirror S10 Toray Plastics). For the embodiments with the polyethylene (PE) backing, the pressure sensitive adhesive solution was coated on a fluoro carbon treated PET liner (2 mil Clear Polyester "S Take off", Loparex, Cary N.C.) for heat treatment and then subsequently laminated on the PE film because the PE film did not have high heat resistance.

TABLE 1

Characteristics of Gas Detection Elements.

| | Mass Quantities (g) | | | | PSA | Backing | Adhesive Thick. |
| --- | --- | --- | --- | --- | --- | --- | --- |
| Element | CC-1 | MEK | BPO | Toluene | PSA Material | Material | (μm) |
| GDE-1 | 2.29 | 15.0 | 0.96 | 26.9 | 72.1 Dow 282 | 1 Mil PI/Kapton | 30 |
| GDE-2 | 2.29 | 15.0 | 0.96 | 26.9 | 72.1 Dow 282 | 1 Mil PI/Kapton | 60 |
| GDE-3 | 2.29 | 15.0 | 0.96 | 26.9 | 72.1 Dow 282 | 1 Mil PI/Kapton | 85 |
| GDE-4 | 2.29 | 15.0 | 0.48 | 26.9 | 72.1 Dow 282 | 1 Mil PI/Kapton | 85 |
| GDE-5 | 2.29 | 15.0 | 0.24 | 26.9 | 72.1 Dow 282 | 1 Mil PI/Kapton | 85 |
| GDE-6 | 2.29 | 15.0 | 0.0 | 26.9 | 72.1 Dow 282 | 1 Mil PI/Kapton | 85 |

TABLE 1-continued

Characteristics of Gas Detection Elements.

| Element | Mass Quantities (g) | | | | PSA | PSA Material | Backing Material | Adhesive Thick. (μm) |
|---|---|---|---|---|---|---|---|---|
| | CC-1 | MEK | BPO | Toluene | | | | |
| GDE-7 | 2.29 | 15.0 | 0.96 | 26.9 | 72.1 | Dow 282 | 2 Mil FEP/Teflon | 30 |
| GDE-9 | 2.29 | 10.4 | 1.0 | 28.0 | 75.0 | Mom. PSA518 | 1 Mil PI/Kapton | 30 |
| GDE-10 | 2.29 | 10.4 | 1.0 | 28.0 | 75.0 | Mom. PSA518 | 1 Mil PI/Kapton | 60 |
| GDE-11 | 2.29 | 10.4 | 1.0 | 28.0 | 75.0 | Mom. PSA518 | 1 Mil PI/Kapton | 85 |
| GDE-12 | 2.29 | 10.4 | 1.0 | 28.0 | 75.0 | Mom. PSA518 | 2 Mil FEP/Teflon | 30 |
| GDE-13 | 2.29 | 10.4 | 1.0 | 28.0 | 75.0 | Mom. PSA518 | 2 Mil FEP/Teflon | 30 |
| GDE-14 | 2.29 | 10.4 | 1.0 | 28.0 | 75.0 | Mom. PSA518 | 1 Mil PE | 30 |
| GDE-15 | 2.29 | 10.4 | 1.0 | 28.0 | 75.0 | Mom. PSA518 | 1 Mil PET/Mylar | 30 |
| GDE-16 | 1.70 | 7.7 | 1.0 | 28.0 | 75.0 | Mom. PSA518 | 1 Mil PI/Kapton | 30 |
| GDE-17 | 1.87 | 8.5 | 1.0 | 28.0 | 75.0 | Mom. PSA518 | 1 Mil PI/Kapton | 20 |
| GDE-18 | 1.87 | 8.5 | 1.0 | 28.0 | 75.0 | Mom. PSA518 | 1 Mil PI/Kapton | 40 |
| GDE-19 | 2.29 | 10.4 | 1.0 | 28.0 | 75.0 | Mom. PSA518 | 1 Mil PI/Kapton | 15 |
| GDE-20 | 2.29 | 10.4 | 1.0 | 28.0 | 75.0 | Mom. PSA518 | 1 Mil PI/Kapton | 45 |
| GDE-21 | 2.71 | 12.3 | 1.0 | 28.0 | 75.0 | Mom. PSA518 | 1 Mil PI/Kapton | 20 |
| GDE-22 | 2.71 | 12.3 | 1.0 | 28.0 | 75.0 | Mom. PSA518 | 1 Mil PI/Kapton | 40 |
| GDE-23 | 2.88 | 13.1 | 1.0 | 28.0 | 75.0 | Mom. PSA518 | 1 Mil PI/Kapton | 30 |
| GDE-24 | 2.29 | 10.4 | 1.0 | 28.0 | 75.0 | Mom. PSA518 | 2 Mil Acrylic/UVA | 30 |

Comparative Example 2.1: Comparative Elements

Fabrication of Comparative Element #1.

Creating Treatment Liquid:

The treatment liquid was created by adding benzoyl peroxide (1.115 g, 97%, Luperox® A98, Aldrich) to one part of a two-part gas permeable acrylic (100 g, ORIBAIN BPS4891TX, Toyo Ink) and stirred by hand for 3 minutes to form a treatment liquid. A chemochromic composition was created by dispersing CC-1 (2.29 g) in methyl ethyl ketone (15 g, Aldrich) making sure to break up any large chunks to create a dispersion. The chemochromic composition was then added to the treatment liquid and mixed by hand until uniform, about 3 minutes. The result was a coating mixture.

Coating the Pressure Sensitive Adhesive on the Backing:

The resulting coating mixture was then film coated using bar applicator (SA-210, Baker-Type-Applicator, Tester Sangyo Co., Ltd.) on a 30 cm×40 cm polyimide backing (1 mil, Kapton, Dupont) with the dial set to the desired wet pressure sensitive adhesive thickness. The coating mixture was placed in front of the applicator and the applicator was then pulled across the backing coating it as it progressed. The result was a coated backing.

Removing Solvent and Curing Pressure Sensitive Adhesive:

The coated backing was then air dried at 25° C. for 30 seconds to remove the solvent. Next, the coated backing was then cured in an oven at 177° C. for 3 minutes. The result was a comparative gas detection element (CGDE-1).

Comparative Example 2.2: Comparative Elements

Fabrication of Additional Comparative Elements

Additional comparative gas detection elements were fabricated using a method similar to those in Comparative Example 2.2 with the exception of the change outlined in Table 2.

TABLE 2

Characteristics of the Comparative Gas Detection Elements.

| Element | Mass Quantities (g) | | | | PSA | PSA Material | Backing Material | Adhesive Thick. (μm) |
|---|---|---|---|---|---|---|---|---|
| | CC-1 | MEK | BPO | Toluene | | | | |
| CGDE-1 | 2.53 | 15.0 | 1.12 | — | 100.0 | Toyo 4891TX | 1 Mil PI/Kapton | 30 |
| CGDE-2 | 2.53 | 15.0 | 1.12 | — | 100.0 | Toyo 4891TX | 1 Mil PI/Kapton | 60 |
| CGDE-3 | 2.53 | 15.0 | 1.12 | — | 100.0 | Toyo 4891TX | 1 Mil PI/Kapton | 85 |

TABLE 2-continued

Characteristics of the Comparative Gas Detection Elements.

| Element | Mass Quantities (g) | | | | PSA | Backing | Adhesive |
| | CC-1 | MEK | BPO | Toluene | PSA Material | Material | Thick. (μm) |
|---|---|---|---|---|---|---|---|
| CGDE-4 | 2.53 | 15.0 | 1.12 | — | 100.0 Toyo 4891TX | 2 Mil FEP/Teflon | 30 |

Example 3.1: Characterization of Experimental Results

Characterization of Premature Reactivity.

All gas detection elements were qualitatively assessed to determine the possibility of premature color-change due to the reaction of the chemochromic composition with residual radicals in the polymer matrix of the pressure sensitive adhesive. The embodiments were examined immediately after curing with a color analyzer (PCM+, ColorTec, Clinton, N.J. USA). When required, the color analyzer was calibrated with a standard white panel included with the unit. In addition, some embodiments were also exposed to a UV accelerated exposure conditions and their color was measured afterwards. The results are presented in Table 3. In general, it is shown that trace amounts of radicals appear to be coming from the free radical transfer reaction generated by benzoyl peroxide initiator. When the amount of benzoyl peroxide initiator decreases below adequate levels, there appears to be less hydrogen chemochromic activation. In general, for all embodiments, the results show that trace amounts of radicals due to crosslinking can pre-activate the chemochromic composition in larger dimension polymer matrices as seen by comparing CGDE-3, which has a thickness of 85 microns versus CGDE-1, which has a thickness of 30 microns, or CGDE-2, which has a thickness of 60 microns. While not wanting to be limited by theory, it is thought that the ability of air (oxygen) to permeate the polymer matrix prevents radical reaction on active sites of chemochromic reagent and makes the chemochromic reagent's active sites less susceptible to false indications. However, in thicker geometries the air (oxygen) adsorption in the center of the material is slow and results in the activation of the chemochromic reagent. It was also noted that the presence of ultraviolet radiation may lead to the creation of trace radical in the matrix, causing premature chemochromic activation.

Test results of UV exposure showed the possibility of premature chemochromic activation by radicals that were generated in the backing layer. Silicone, polyimide, and FEP have inherent UV resistance. Acrylic adhesive does not have UV resistance and when exposed to UV, it generates radicals. Polyimide stops UV in its layer. Sample CGDE-1 did not show premature color change because UV was stopped by polyimide. FEP does not stop UV, although fluoro carbon polymer itself is stable under UV. Regarding sample CGDE-4, UV passed through FEP and reacted with acrylic adhesive, generating radicals and causing premature chemochromic activation. Regarding sample GDE-15, PET backing reacted with UV and generated radicals. These radicals moved and prematurely activated the chemochromic pigment in the silicone adhesive layer (i.e. the gas detection layer). As a result, premature color change was observed even though the silicone adhesive has UV resistance. GDE-24 has PET film backing that contains a UV absorber (2 mil PET, Toray Lumirror U-65V) and it did not release radicals into the silicone adhesive layer. Radicals were absorbed by the UV absorber. As a result, there was no premature color change of GDE-24.

As shown here, UV resistant backing (where radicals are not generated when the backing is exposed to UV) is necessary to be used for this gas sensing element.

It is well known that fluoro carbon polymer films are stable against UV, but are not capable of stopping UV.

The same results would be expected with other fluoro carbon polymer films like PFA (tetra fluoro ethylene per fluoro alkylvivyl ether copolymer), ETFE (tetra fluoro ethylene hexa fluoro ethylene copolymer), and PTFE (poly tetra fluoro ethylene).

It is well known that HALS (Hindered Amine Light Stabilizers) also has radical scavenging properties.

Regarding GDE-14, premature color change was not observed with PE backing in this test.

Polyethylene does not have a functional group or unsaturated bonding and hence it is relatively strong against UV.

TABLE 3

Shelf Performance of Select Gas Detection Elements during Curing and during UV-Irradiation.

| Element | Initiator (BPO) | PSA Material | Backing Material | Adhesive Thick. (μm) | Chemochromic activation at curing | Chemochromic activation during UV Exposure |
|---|---|---|---|---|---|---|
| CGDE-1 | 1.12 g | Toyo 4891TX | 1 Mil PI/Kapton | 30 | ○ | ○ (backing) |
| CGDE-2 | 1.12 g | Toyo 4891TX | 1 Mil PI/Kapton | 60 | ○ | — |
| CGDE-3 | 1.12 g | Toyo 4891TX | 1 Mil PI/Kapton | 85 | ● | — |
| CGDE-4 | 1.12 g | Toyo 4891TX | 2 Mil FEP/Teflon | 30 | ○ | ● (backing) |
| GDE-1 | 0.96 g | Dow 282 | 1 Mil PI/Kapton | 30 | ○ | ○ (backing) |
| GDE-2 | 0.96 g | Dow 282 | 1 Mil PI/Kapton | 60 | ● | — |
| GDE-3 | 0.96 g | Dow 282 | 1 Mil PI/Kapton | 85 | ● | — |
| GDE-4 | 0.48 g | Dow 282 | 1 Mil PI/Kapton | 85 | ◎ | — |

TABLE 3-continued

Shelf Performance of Select Gas Detection Elements during Curing and during UV-Irradiation.

| Element | Initiator (BPO) | PSA Material | Backing Material | Adhesive Thick. (μm) | Chemochromic activation at curing | Chemochromic activation during UV Exposure |
|---------|-----------------|--------------|------------------|----------------------|-----------------------------------|---------------------------------------------|
| GDE-5 | 0.24 g | Dow 282 | 1 Mil PI/Kapton | 85 | ◯ | — |
| GDE-6 | 0 g | Dow 282 | 1 Mil PI/Kapton | 85 | ◯ | — |
| GDE-7 | 0.96 g | Dow 282 | 2 Mil FEP/Teflon | 30 | ◯ | — |
| GDE-9 | 1.00 g | Mom. PSA518 | 1 Mil PI/Kapton | 30 | ◯ | ◯ (backing) |
| GDE-10 | 1.00 g | Mom. PSA518 | 1 Mil PI/Kapton | 60 | ◯ | — |
| GDE-11 | 1.00 g | Mom. PSA518 | 1 Mil PI/Kapton | 85 | ◯ | — |
| GDE-12 | 1.00 g | Mom. PSA518 | 2 Mil FEP/Teflon | 30 | ◯ | ◯ (backing) |
| GDE-13 | 1.00 g | Mom. PSA518 | 2 Mil FEP/Teflon | 30 | ◯ | ◯ (adhesive) |
| GDE-14 | 1.00 g | Mom. PSA518 | 1 Mil PE | 30 | ◯ | ◯ (backing) |
| GDE-15 | 1.00 g | Mom. PSA518 | 1 Mil PET/Mylar | 30 | ◯ | ● (backing) |
| GDE-24 | 1.00 g | Mom. PSA518 | 2 Mil PET/UVA | 30 | ◯ | ◯ (backing) |

Notes:
UVA:- Backing also comprises a UV Absorber,
◯: No activation of chemochromic pigment
●: Chemochromic pigment was activated completely (Color was changed)
◉: Chemochromic pigment was activated partially (Color was changed, but not fully)
—: Not tested
(backing): UV was irradiated from backing side
(adhesive): UV was irradiated from adhesive side
2 Mil PET/UVA is Toray Lumirror U-65V Example 3.2 Effect of Release Liner GDE-9 was produced in a scaled up size of 600 mm width×100 yds and then wound up on one core to make a bundle roll.

When this bundle roll was stored in a warehouse for 7 days at ambient conditions, the color of the adhesive inside of the bundle roll layers had prematurely changed into black. This chemochromic activation occurred due to residual radicals from the crosslinking step and due to an insufficient supply of air (oxygen) because the second surface of the gas detection layer was adhered on the second surface of the backing.

In this situation, no ambient air (oxygen) can penetrate into the gas detection element, hence causing this premature chemochromic activation.

On the other hand, when GDE-9 was laminated with a release liner on the gas detection layer and the gas detection element was wound up into a bundle roll, premature color-change (chemochromic activation) inside of the bundle roll layers was not observed. The presence of the release liner caused a gap or space to be created between the backing and the release liner, allowing air (oxygen) to penetrate in. The release liner is 2 mil PET (2 mil clear Polyester "S Take off" from Loparex) coated with fluoro Si release agent. 2 mil PET seems to have sufficient air (oxygen) permeability to avoid premature chemochromic activation.

Example 3.3 Characterization of Experimental Results

Characterization of Sensitivity to Hydrogen.

To determine the timeframe for exposure, a selected embodiment of gas detection elements were measured to determine their color change response to the presence of hydrogen gas as a function of time. The color of the embodiments was measured with a color analyzer (PCM+, ColorTec Associates, Inc.) before exposure to hydrogen gas. The color was recorded. When required, the color analyzer was calibrated with a standard white panel included with the unit. After initial measuring the samples were placed in the test setup. Then the embodiments were each mounted to a flexible PTFE frame small enough to be placed in a 30 mL glass vial. The vial had a lid with an inlet port and an exhaust port so that it could be sealed and the inlet port connected in fluid communication to a source of gas and an exhaust port vent. Then, after the mounted sample was placed in the glass vial and sealed, 100% $H_2$ gas at 6 mL/min at room temperature was then flowed through the vial for 1 minute. After 1 minute, the gas flow was stopped, the vial vented, and the sample removed. After removal, the sample was then re-measured with the color analyzer (PCM+, ColorTec) to determine its color. The color change ($\Delta L^*$) was then calculated as the difference between the color after exposure and the color before exposure. The experiment was re-run with new samples of the same embodiment at times of 1.5 minutes, 2 minutes, 2.5 minutes, 5 minutes, and 20 minutes. A total of three samples were run for each time with the exception of the 5 minute sample and the 20 minute sample, where a single sample was run. The single control sample was not exposed. The sample exposed to five minutes of hydrogen had a color change that was greater than 5. Requiring a color change of equal or greater than 5 upon detection requires indicating performance of at least this order so that the color change is easy to recognize. This experiment also showed that the majority of color change occurred in the samples after 5 minutes of exposure to 100% $H_2$ gas at 6 mL/min at room temperature.

In addition, samples of embodiment GDE-9, an embodiment with a SilGrip*® PSA518 polymer matrix with a 5.5 wt % pigment to silicone PSA solids ratio, was tested to find when the samples turned the maximum color. The procedure is the same as above with the exception that the single samples were measured after exposure at varying lengths of time for varying flow rates and concentrations of $H_2$ gas as in Table 4. As shown in the table, at 100% $H_2$ gas at 6 mL/min an exposure of 5 minutes, Test A-3, would result in a color change comparable to the full color change as if the sample were left exposed for a longer period of time, or Test A-4.

mL glass vial. After the mounted sample was placed in the glass vial and sealed, 100% $H_2$ gas at 6 mL/min at room temperature was then flowed through the vial for 5 minutes. After 5 minutes, the gas flow was stopped, the vial vented,

TABLE 4

Examination of Time to Maximum Color Change as a Function of $H_2$ Gas Concentration and Flow Rate for GDE-9.

| Test # | Temp (° C.) | $H_2$ Gas Concentration | Flowrate (mL/min) | Exposure Time (min) | $L^*_{Initial}$ | $L^*_{final}$ | $\Delta L^*$ |
|---|---|---|---|---|---|---|---|
| A-1 | 25 | 100% $H_2$ | 6 | 2 | 34.80 | 51.31 | 16.51 |
| A-2 | 25 | 100% $H_2$ | 6 | 2.5 | 34.80 | 51.26 | 16.46 |
| A-3 | 25 | 100% $H_2$ | 6 | 5 | 34.80 | 52.37 | 17.57 |
| A-4 | 25 | 100% $H_2$ | 6 | 20 | 34.80 | 50.97 | 16.17 |
| B-1 | 25 | 1% $H_2/N_2$ | 6 | 85 | 34.80 | 50.17 | 15.37 |
| B-2 | 25 | 1% $H_2/N_2$ | 9 | 30 | 34.80 | 50.47 | 15.67 |
| B-3 | 25 | 1% $H_2/N_2$ | 18 | 30 | 34.80 | 51.50 | 16.70 |
| B-4 | 25 | 1% $H_2/N_2$ | 17 | 60 | 34.80 | 51.61 | 16.81 |
| B-5 | 25 | 1% $H_2/N_2$ | 13 | 85 | 34.80 | 49.14 | 14.34 |
| B-6 (Ex.) | 25 | 1% $H_2/N_2$ | 65 | 3 | 34.80 | ~50.00 | ~15.20 |
| C-1 | 25 | 0.01% $H_2/N_2$ | 18 | 60 | 35.32 | 41.84 | 6.52 |
| C-2 | 25 | 0.01% $H_2/N_2$ | 18 | 75 | 35.32 | 46.36 | 11.04 |
| C-3 | 25 | 0.01% $H_2/N_2$ | 13 | 90 | 35.32 | 44.72 | 9.40 |
| C-4 | 25 | 0.01% $H_2/N_2$ | 9 | 120 | 35.32 | 41.14 | 5.82 |
| C-5 | 25 | 0.01% $H_2/N_2$ | 6 | 240 | 35.32 | ~35.32 | — |
| D-1 | 25 | 3% H2/Air | 100 | 60 | 36.39 | 45.31 | 8.92 |
| D-2 | 25 | 2% H2/Air | 100 | 120 | 36.39 | 41.76 | 5.37 |
| D-3 | 25 | 2% H2/Air | 100 | 360 | 36.39 | 46.86 | 10.47 |
| D-4 | 25 | 1% H2/Air | 100 | 1440 | 35.74 | 42.76 | 7.02 |
| D-5 | 25 | 1% H2/Air | 100 | 1920 | 35.74 | 45.28 | 9.54 |
| E-1 | 25 | 3% H2/Air | 25 | 120 | 36.39 | 41.91 | 5.52 |
| E-2 | 25 | 3% H2/Air | 100 | 120 | 36.39 | 46.69 | 10.3 |

(Ex) - indicates data point extrapolated by examination of other data.

Example 3.4: Characterization of Experimental Results

Examination of Element Performance/Sensitivity to Hydrogen.

The gas detection elements were measured to determine their color change response to the presence of hydrogen gas. The color of the embodiments was measured with a color analyzer (PCM+, ColorTec Associates, Inc.). The color was recorded. When required the color analyzer was calibrated with a standard white panel included with the unit. After initial measuring the samples were placed in the test setup described in Example 3.2. The embodiments were mounted to a flexible PTFE frame small enough to be placed in the 30 mL glass vial. After the mounted sample was placed in the glass vial and sealed, 100% $H_2$ gas at 6 mL/min at room temperature was then flowed through the vial for 5 minutes. After 5 minutes, the gas flow was stopped, the vial vented, and the sample removed. After removal, the sample was then re-measured with the color analyzer (PCM+, ColorTec Associates, Inc.) to determine its color. The color change ($\Delta L^*$) was then calculated as the difference between the color after exposure and the color before exposure. In order to recognize color change easily, the value of the color change needs to be at least 5. The results for selected embodiments are shown in Table 5. As shown, all elements tested met the criteria when exposed to an oxygen-containing gas, or air, as part of the fabrication process in order to protect the pigment from premature activation.

TABLE 5

$H_2$ Performance Results for Selected Elements.

| Type | wt % Pigment to Silicone Solids | Thick. (μm) | Actual Thick. (μm) | $L^*_{Initial}$ | $L^*_{final}$ | Avg. $L^*_{final}$ | $\Delta L^*$ | Meet Criteria ? |
|---|---|---|---|---|---|---|---|---|
| GDE-16 | 4.09 | 30 | 32 | 37.97 | 49.74 | 50.38 | 12.41 | Yes |
|  |  |  | 31 |  | 51.02 |  |  |  |
| GDE-17 | 4.5 | 20 | 18 | 36.76 | 41.54 | 42.27 | 5.51 | Yes |
|  |  |  | 18 |  | 42.99 |  |  |  |
| GDE-18 | 4.5 | 40 | 42 | 39.32 | 55.52 | 55.75 | 16.43 | Yes |
|  |  |  | 41 |  | 55.98 |  |  |  |
| GDE-19 | 5.5 | 15 | 17 | 36.61 | 47.21 | 47.52 | 10.91 | Yes |
|  |  |  | 17 |  | 47.82 |  |  |  |
| GDE-9 | 5.5 | 30 | 27 | 36.76 | 53.03 | 53.00 | 16.24 | Yes |
|  |  |  | 27 |  | 52.96 |  |  |  |
| GDE-9 | 5.5 | 30 | 26 | 38.49 | 52.07 | 52.74 | 14.25 | Yes |
|  |  |  | 27 |  | 53.40 |  |  |  |
| GDE-9 | 5.5 | 30 | 27 | 37.86 | 52.30 | 52.36 | 14.50 | Yes |
|  |  |  | 26 |  | 52.42 |  |  |  |

TABLE 5-continued

H₂ Performance Results for Selected Elements.

| Type | wt % Pigment to Silicone Solids | Thick. (μm) | Actual Thick. (μm) | L*$_{Initial}$ | L*$_{final}$ | Avg. L*$_{final}$ | ΔL* | Meet Criteria ? |
|---|---|---|---|---|---|---|---|---|
| GDE-20 | 5.5 | 45 | 42 | 41.14 | 57.67 | 58.07 | 16.93 | Yes |
|  |  |  | 41 |  | 58.46 |  |  |  |
| GDE-21 | 6.5 | 20 | 20 | 36.83 | 51.34 | 51.45 | 14.62 | Yes |
|  |  |  | 21 |  | 51.55 |  |  |  |
| GDE-22 | 6.5 | 40 | 42 | 42.05 | 59.05 | 59.25 | 17.20 | Yes |
|  |  |  | 43 |  | 59.45 |  |  |  |
| GDE-23 | 6.91 | 30 | 31 | 40.30 | 56.83 | 57.00 | 16.70 | Yes |
|  |  |  | 30 |  | 57.17 |  |  |  |

Example 4.1 Manufacturing of Gas Detection Element

By the following method, a gas detection element (hereinafter referred to as "GDE-A") including chemochromic pigment particles was manufactured.

The gas detection element had a configuration including a backing material, a primer layer, and a gas detection layer including chemochromic pigment particles (also referred to as an "adhesive layer"), in the stated order.

As the backing material, polyimide (Kapton) (Dupont High Performance Films Circleville, Ohio, USA) having an area size of 30 cm×40 cm and a thickness of 1 mil was used.

The primer layer was formed by the following method.

A polysiloxane (SilGrip* SS4195A-D1, Momentive) including 15.06 g of a methylphenylsiloxane group was dissolved in 96.61 g of xylene at room temperature, and was then sufficiently stirred, to obtain a uniform solution. In the stirring state, 0.34 g of a cross-linking agent (SilForce* SS4191B, Momentive) was added to this solvent, and the solvent was further stirred for several minutes. Next, 0.567 g of an accelerator (SilForce* SS4259C, Momentive), and 0.567 g of a catalyst (SilForce* SS4192C, Momentive) were sequentially added, and the solvent was stirred for several minutes. Accordingly, a coating liquid for the primer layer (U-1) was obtained.

As the chemochromic pigment particles, the chemochromic pigment element CC-1 prepared in Example 1.1 above was used. 2.39 g of CC-1 was sufficiently dispersed in 10.4 g of methyl ethyl ketone (Aldrich), to fabricate a chemochromic dispersion liquid.

The coating mixture for the gas detection layer was prepared by the following method.

First, 1.0 g of benzoyl peroxide (97%, Luperox® A98, Aldrich) was added to 10 g of toluene (Aldrich). The obtained solvent was stirred for one minute, to completely dissolve the benzoyl peroxide.

Next, all of this solvent and 18 g of toluene (Aldrich) were added to 75 g of an adhesive precursor (SilGrip*® PSA518, Momentive), and this was stirred for three minutes. Accordingly, a treatment liquid was fabricated.

Next, in the obtained treatment liquid, 12.79 g of the above chemochromic composition was added, and was sufficiently stirred until a uniform liquid was obtained.

Accordingly, a coating mixture (C-1) was obtained.

The gas detection element was fabricated as follows.

First, on a backing material, a coating liquid (U-1) for the primer layer having a thickness of approximately 0.5 μm was coated. Subsequently, this was dried at a temperature of 120° C. for 1 min, and a primer layer was formed.

Next, a bar coater (SA-210, Baker-Type-Applicator, Tester Sangyo Co., Ltd., Saitama-Ken, Japan) was used to coat the primer layer with the coating mixture (C-1).

Next, the backing material coated by the primer layer and the coating mixture, was dried between 30 seconds to 3 minutes at 25° C., to remove the solvent. Next, this backing material was retained in an oven for 3 minutes at 177° C. Accordingly, the gas detection element (GDE-A) was obtained.

The following table 6 schematically indicates the specifications of the configuration of the gas detection element (GDE-A).

TABLE 6

Configuration of Gas Detection Element

| | Gas Detection Layer | | | | | | |
|---|---|---|---|---|---|---|---|
| | Mass Quantities (g) | | | | PSA | Thickness | Backing |
| Element | CC-1 | MEK | BPO | Toluene | PSA Material | (μm) | Material |
| GDE-A | 2.39 | 10.4 | 1.0 | 28.0 | 75.0 Mom. PSA518 | 35 | 1 Mil PI/Kapton |

Comparative Example 4.2 Manufacturing of Gas Detection Element

By the following method, a gas detection element (hereinafter referred to as "GDE-B") including chemochromic pigment particles was manufactured.

The gas detection element had a configuration in which a gas detection layer including chemochromic pigment particles was set on a backing material.

As the backing material, a polyethylene film (U-LineS1113, nominal thickness 2 Mil) having a size of 30 cm×40 cm and a thickness of 45 μm was used.

The gas detection layer was formed as follows.

2.9 g of the chemochromic pigment element CC-1 was added into 10 g of a silicone sealant (Dow Corning® 734 Flowable Sealant), and this mixture was sufficiently stirred.

This mixture was applied on the backing material, and was dried for 24 hours at room temperature. Accordingly, a gas detection layer having a thickness of approximately 200 µm was formed on the backing material.

(Evaluation)

The two types of gas detection elements (GDE-A and GDE-B) described above were evaluated for the adhesion of the gas detection layers.

The adhesion of the gas detection layers was evaluated according to a 180° peel strength test using the following method.

Measurement samples were fabricated wherein the gas detection elements (GDE-A and GDE-B) were cut into a size of a width of 1 inch and a length of 18 inches. In the following paragraphs, a measurement sample obtained from the gas detection element GDE-A is referred to as "sample A". A measurement sample obtained from the gas detection element GDE-B is referred to as "sample B".

Next, in atmospheric air with a temperature of 23° C. and a relative humidity of 50% RH, on a stainless steel sheet (Type 304), the samples were placed such that the gas detection layer is facing downward. Next, on the sample, a rubber roller weighing 2 kg was moved back and forth once, to pressure bond the sample on the surface of the stainless steel sheet. After the pressure bonding, the following test was performed within one minute.

Next, a tensile testing machine (5565PA656, or 33R 4465P4758, Instron corp.) was used to perform the 180° peel strength test on each sample. The adhesion angle was 180°, and the tensile speed was 300 mm/minute.

Note that the above evaluation was performed in compliance with ASTM D 3330, Method D.

As a result, the adhesion of the sample A was 4.9 N/25 mm. On the other hand, the sample B came off immediately, and the adhesion could not be measured.

Note that as the target of pressure bonding, instead of a sole stainless steel sheet, a stainless steel having a paint (All Surface Enamel High Gloss 6509-00715 Safety Yellow, The Sherwin Williams Company) applied was used, and the same evaluation was made. As a result, the adhesion of the sample A was 5.5±1.0 N/25 mm. On the other hand, the sample B came off immediately, and the adhesion could not be measured.

Furthermore, the same evaluation was carried out by using a polyimide film as the target of pressure bonding. The target of pressure bonding was formed by placing a polyimide film having a thickness of 0.025 mm on the surface of the aforementioned stainless steel sheet, via an adhesive.

The sample A was placed on the surface of the polyimide film so that the gas detection layer faced the polyimide film, and a roller was moved back and forth once over the backing side of the sample A with a load of 2 kg. Accordingly, the sample A was adhered to the polyimide film, and a test specimen was formed.

As a result of measurement using this test specimen, the adhesion of the sample A was 4.4 N/25 mm. Note that in this experiment, it was confirmed that peeling occurred between the polyimide film and the sample A.

Next, a similar evaluation was carried out by using other gas sensing elements C and D.

The gas sensing element C was fabricated by the same method as that of the aforementioned GDE-A. However, the coating mixture for the gas detection layer was prepared by the following method.

20 g of SPUR+* PSA 3.0 (Momentive urethane silicone hybrid condensation crosslinking type solid content 40%) and 100 g of ethyl acetate were stirred and mixed to obtain a solution. 0.46 g of CC-1 was dispersed in 5 g of MEK and this was mixed with the above solution. Accordingly, a coating mixture for the gas detection layer was prepared.

The other steps are the same as those of the aforementioned GDE-A.

On the other hand, the gas detection element D was also manufactured by the same method as the aforementioned GDE-A. However, the coating mixture for the gas detection layer was prepared by the following method.

In 35 g of SilGrip* PSA 6574 (Momentive peroxide crosslinked silicone), 0.5 g of benzoyl peroxide dissolved in 13 g of toluene, was stirred and mixed, to obtain a solution. 1.1 g of CC-1 was dispersed in 5 g of MEK and this was mixed with the above solution. Accordingly, a coating mixture for the gas detection layer was prepared.

The other steps are the same as those of the aforementioned GDE-A.

Samples C and D were fabricated from the gas sensing elements C and D, respectively, and were evaluated, by the same method as described above. The target of pressure bonding was a stainless steel sheet.

As a result of the measurement, the adhesion of sample C was 1.4 N/25 mm. The adhesion of sample D was 5.3 N/25 mm.

While various disclosed embodiments have been described above, it should be understood that they have been presented by way of example only, and not limitation. Numerous changes to the subject matter disclosed herein can be made in accordance with this disclosure without departing from the spirit or scope of this disclosure. In addition, while a particular feature may have been disclosed with respect to only one of several implementations, such feature may be combined with one or more other features of the other implementations as may be desired and advantageous for any given or particular application. Thus, the breadth and scope of the subject matter provided in this disclosure should not be limited by any of the above explicitly described embodiments. Rather, the scope should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. Notwithstanding that the numerical ranges and parameters are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. Groupings of alternative elements or embodiments disclosed herein are not to be construed as limitations. Each group member may be referred to and claimed individually or in any combination with other members of the group or other elements found herein. Furthermore, not all illustrated acts or events are required to implement a methodology disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are hot limited to embodiments precisely as shown and described.

The invention claimed is:

1. A gas sensing element comprising:
a gas detection layer including a pigment,
wherein the gas detection layer includes a silicone-based pressure sensitive adhesive that has an adhesion of greater than or equal to 0.2 N/25 mm,
wherein the silicone-based pressure sensitive adhesive includes a polymer of siloxane having at least a methylphenylsiloxy group or a dimethylsiloxy group, and
wherein the pigment includes a chemochromic composition such that the chemochromic composition is dispersed within the polymer of siloxane and, upon the gas detection layer being pressed against a target other than the gas sensing element itself, the gas sensing element is adhered to the target by the adhesion of the silicone-based pressure sensitive adhesive.

2. The gas sensing element of claim 1, wherein the pigment irreversibly changes in color, by contacting reducing gas.

3. The gas sensing element of claim 1, the element further comprising carrier particles having a surface, the pigment including a palladium oxide, palladium hydroxide, or palladium salts on the surfaces of carrier particles.

4. The gas sensing element of claim 3, wherein a noble metal other than palladium is supported or loaded, on the surfaces of the carrier particles.

5. The gas sensing element of claim 3, wherein the carrier particles include titanium oxide.

6. The gas sensing element of claim 1, further comprising:
a backing material.

7. The gas sensing element of claim 6, wherein the backing material includes polyimide; polyethylene; fluoro carbon polymer such as fluorinated ethylene propylene copolymer (FEP), ethylene tetrafluoroethylene copolymer (ETFE), poly tetra fluoro ethylene (PTFE), or tetra fluoro ethylene hexa fluoro propylene copolymer (PFA); or polyethylene terephthalate (PET) which contains UV absorber or hindered amine light stabilizers (HALS).

8. The gas sensing element of claim 1, wherein the gas sensing element is rolled up into a bundle roll-shape.

9. The gas sensing element of claim 1, wherein, in a manufacturing process, the gas detection layer is exposed to an oxygen-containing atmosphere.

10. The gas sensing element of claim 1, wherein the gas detection layer has a release liner on a finished product or on a product that is in process of production.

11. A method for producing the gas sensing element of claim 1, the method comprising:
(1) contacting a treatment liquid and the chemochromic composition, the treatment liquid comprising a siloxane precursor and an initiator; and
(2) heating the treatment liquid to a temperature sufficient to activate the initiator so that the precursor is crosslinked to create the gas detection layer.

12. The method of claim 11, where the chemochromic composition comprises one or more palladium-oxide-based chemochromic elements.

13. The method of claim 12, wherein the gas sensing element includes backing that is resistant to ultraviolet radiation.

14. The method of claim 12, further comprising the step of exposing the gas detection layer to an oxygen-containing atmosphere.

15. The method of claim 14, wherein the step of exposing the gas detection layer to an oxygen-containing atmosphere comprises using an oxygen permeable release liner.

* * * * *